(12) United States Patent
Kim et al.

(10) Patent No.: US 11,772,304 B2
(45) Date of Patent: Oct. 3, 2023

(54) IMPLANT FOR IMPLANTATION INTO HUMAN BODY AND MANUFACTURING METHOD THEREOF

(71) Applicants: UNIVERSITY OF ULSAN FOUNDATION FOR INDUSTRY COOPERATION, Ulsan (KR); THE ASAN FOUNDATION, Seoul (KR)

(72) Inventors: Nam Kug Kim, Seoul (KR); Guk Bae Kim, Seoul (KR); Sang Wook Lee, Seoul (KR); Beom Seok Ko, Seoul (KR); Jong Won Lee, Seoul (KR); Sei Hyun Ahn, Seoul (KR)

(73) Assignees: UNIVERSITY OF ULSAN FOUNDATION FOR INDUSTRY COOPERATION, Ulsan (KR); THE ASAN FOUNDATION, Seoul (KR)

( * ) Notice: Subject to any disclaimer, the term of this patent is extended or adjusted under 35 U.S.C. 154(b) by 675 days.

(21) Appl. No.: 16/468,667

(22) PCT Filed: Dec. 12, 2017

(86) PCT No.: PCT/KR2017/014578
§ 371 (c)(1),
(2) Date: Aug. 7, 2019

(87) PCT Pub. No.: WO2018/110951
PCT Pub. Date: Jun. 21, 2018

(65) Prior Publication Data
US 2019/0344480 A1    Nov. 14, 2019

(30) Foreign Application Priority Data
Dec. 12, 2016 (KR) .......... 10-2016-0168618

(51) Int. Cl.
*A61F 2/12* (2006.01)
*B29C 44/02* (2006.01)
(Continued)

(52) U.S. Cl.
CPC ............ *B29C 33/3842* (2013.01); *A61F 2/12* (2013.01); *A61L 27/18* (2013.01); *A61L 27/56* (2013.01);
(Continued)

(58) Field of Classification Search
CPC ................. B29C 33/3842; A61F 2/12
See application file for complete search history.

(56) References Cited

U.S. PATENT DOCUMENTS

| 4,573,900 A | * | 3/1986 | Smith .............. B29C 45/43 |
| | | | 425/155 |
| 5,437,824 A | * | 8/1995 | Carlisle .............. A61F 2/0077 |
| | | | 264/102 |

(Continued)

FOREIGN PATENT DOCUMENTS

| CN | 101733907 B | 6/2014 |
| EP | 2623131 A2 | 8/2013 |

(Continued)

OTHER PUBLICATIONS

International Search Report for PCT/KR2017/014578 dated Mar. 16, 2018 from Korean Intellectual Property Office.

(Continued)

*Primary Examiner* — Cachet I Proctor
(74) *Attorney, Agent, or Firm* — Bridgeway IP Law Group, PLLC; Hyun Woo Shin

(57) ABSTRACT

A method for manufacturing an implant for implantation into a human body, includes preparing a mold having an inner space part so as to have an inner shape corresponding to a defective portion in a human body; injecting silicone foam into the space part of the mold; curing the silicone foam while applying pressure to same; and removing the mold.

9 Claims, 2 Drawing Sheets

(51) Int. Cl.
 B29C 33/38 (2006.01)
 B33Y 50/02 (2015.01)
 B33Y 80/00 (2015.01)
 A61L 27/18 (2006.01)
 A61L 27/56 (2006.01)
 B29C 44/42 (2006.01)
 B29K 83/00 (2006.01)
 B29L 31/00 (2006.01)

(52) U.S. Cl.
 CPC .............. *B29C 44/02* (2013.01); *B29C 44/42* (2013.01); *B33Y 50/02* (2014.12); *B33Y 80/00* (2014.12); *A61F 2240/004* (2013.01); *A61L 2430/04* (2013.01); *B29K 2083/00* (2013.01); *B29L 2031/7532* (2013.01)

(56) References Cited

U.S. PATENT DOCUMENTS

| | | | |
|---|---|---|---|
| 5,658,330 | A | 8/1997 | Carlisle et al. |
| 6,315,796 | B1 * | 11/2001 | Eaton .................. A61F 2/02 623/23.67 |
| 6,520,989 | B1 * | 2/2003 | Eaton .................. A61F 2/12 623/4.1 |
| 7,058,439 | B2 * | 6/2006 | Eaton .................. A61F 2/52 600/425 |
| 8,679,570 | B2 * | 3/2014 | Goraltchouk .......... C08J 9/26 427/2.24 |
| 2013/0302510 | A1 | 11/2013 | Yu |

FOREIGN PATENT DOCUMENTS

| | | |
|---|---|---|
| KR | 10-1999-0068467 A | 9/1999 |
| KR | 10-2008-0095023 A | 10/2008 |
| KR | 10-0961679 B1 | 6/2010 |
| KR | 100961679 B1 * | 6/2010 |
| KR | 10-1067483 B1 | 9/2011 |
| KR | 10-2012-0088928 A | 8/2012 |
| WO | 2008/038851 A1 | 4/2008 |
| WO | 2014/047013 A1 | 3/2014 |

OTHER PUBLICATIONS

Dominick V. Rosato et al., "Injection Molding Handbook", Injection molding handbook, Boston, Kluwer Academic, (Jan. 1, 2001), pp. 1-1457, ISBN 978-0-7923-8619-3, XP055363456, full document was not provided.

* cited by examiner

[FIG. 1]
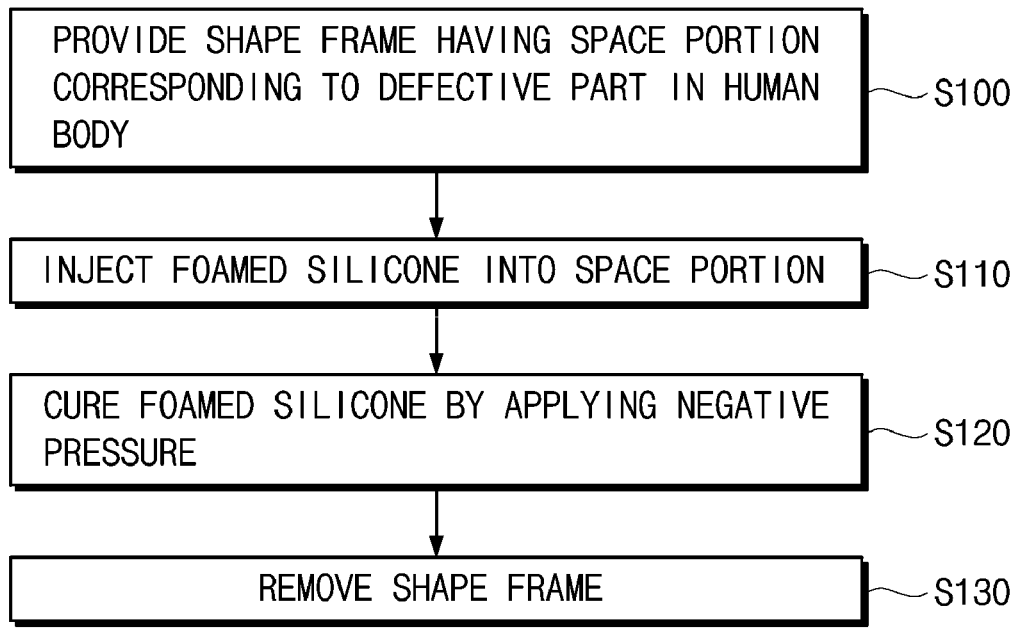

[FIG. 2]
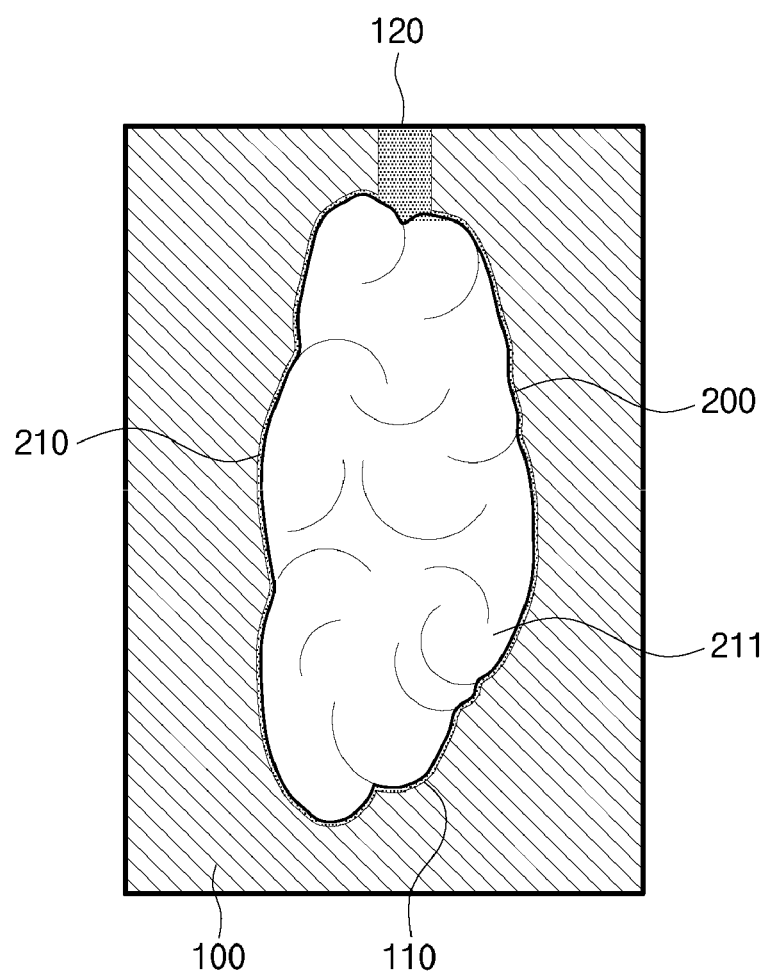

IMPLANT FOR IMPLANTATION INTO HUMAN BODY AND MANUFACTURING METHOD THEREOF

TECHNICAL FIELD

The present invention relates to an implant for an implantation into a human body, which is injected into a body to replace a defective part caused by an operation in a human body, and a method of manufacturing the same.

BACKGROUND ART

In general, during various clinical operations, after lesion tissue or an organ is removed, implants are required to fill in a dead space. In this case, the implants may be made of a material which may be permanently maintained in an inserted state in a human body. Hardness and elasticity of the implants may be adjusted according to the application position and function thereof. In addition, a sense of difference may be minimized, and a risk due to corruption and leakage of a filler filled in the implants may be minimized.

As an example of such implants, in general, an artificial breast implant is used in reconstructive plastic surgery for a breast when breast loss occurs due to diseases such as a cancer or accidents and in cosmetic surgery for a malformed breast. In terms of anatomy, the artificial breast implant is also used for the substitution of organs or tissues.

Such artificial implants are products in which a filling material, such as a saline solution, a hydro-gel, or a silicone gel, is filled in an envelope made of silicone that is implantable to an organ. The artificial implants may be classified into a round type product, and a water drop type (anatomical type) product according to a shape of a product and may be classified into a smooth type product and a texture type product according to surface conditions of a product.

However, in the conventional artificial implant, when the filling material such as the saline solution, the hydro-gel, or the silicone gel is filled in the envelope and the conventional artificial implant is used for a long time or a great force is applied thereto, the filling material leaks into a body due to a rupture of the envelope, resulting in a disease. In addition, the filling material inside the envelope sags by gravity in a state of being installed in the body, and thus, it is difficult to stably maintain a shape of a breast.

Furthermore, since the conventional artificial implant has a structure in which the filling material is filled therein, it is difficult to adjust weight, elasticity, a texture, hardness, and elongation according to the application position and function of the conventional artificial implant in the body, and thus, the conventional artificial implant has a narrow application range.

Such an artificial implant is disclosed in Korean Patent Publication No. 1999-0068467 (Sep. 6, 1999).

DISCLOSURE

Technical Problem

The present invention is directed to provide an implant for an implantation into a human body, which may stably maintaining a shape of a defective part and prevent a disease from occurring due to a filling material leaking into a body, and of which weight, elasticity, a texture, hardness, and elongation may be easily adjusted according to an application position and function in the body, and a method of manufacturing the same.

Technical Solution

The present invention provides a method of manufacturing implant for implantation into the human body, comprising: preparing a mold which of inner cavity corresponds to a defective part in a human body; injecting silicone foam into the mold cavity; curing the silicone foam injected mold under the pressurized condition; and removing the mold.

The preparing a mold includes: modeling a shape to be removed from the human body based on medical images; and manufacturing the mold with the cavity corresponds to the modeled shape.

In the manufacturing of the mold so as to have the inner space corresponding to the modeled shape, the mold may be manufactured using a three-dimensional (3D) printer.

In the injecting silicone foam into the mold cavity, a hardener is added to the said silicone foam; and is mixed in a range of 20 wt % to 80 wt % with respect to a range of 20 wt % to 80 wt % of the said silicone foam.

In the curing the silicone foam injected mold under the pressurized condition, a negative pressure of 0.01 torr to 2100 torr is applied to the said silicone foam for 1 seconds to 300 seconds, and the silicone foam is heated at a temperature of 25° C. to 250° C. to be cured.

In the curing of the silicone foam injected mold under the pressurized condition, when an implant for an implantation into a human body having an elasticity value smaller than a preset reference elasticity value is manufactured, negative pressure lower than preset reference negative pressure is applied, and when an implant for an implantation into a human body having an elasticity value greater than the preset reference elasticity value is manufactured, negative pressure higher than the reference negative pressure is applied.

In the curing of the silicone foam injected mold under the pressurized condition, when an implant for an implantation into a human body having an elasticity value smaller than a preset reference elasticity value is manufactured, a time during which negative pressure is applied is longer than a preset reference time, and when an implant for an implantation into a human body having an elasticity value greater than the reference elasticity value is manufactured, a time during negative pressure is applied is shorter than the preset reference time.

In the curing of the silicone foam injected mold under the pressurized condition, when an implant for an implantation into a human body having increased ductility and elongation is manufactured, negative pressure higher than preset reference negative pressure is applied, and when an implant for an implantation into a human body having decreased ductility and elongation is manufactured, negative pressure lower than the preset reference negative pressure is applied.

The present invention provides an implant for an implantation into a human body which is manufactured according the above-described method of manufacturing the implant for the implantation into the human body.

Advantageous Effects

According to an implant for an implantation into a human body and a method of manufacturing the same according to the present invention, after silicone foam is injecting into the mold, negative pressure or positive pressure is applied to form a bubble inside the silicone foam. When a mixing ratio of the silicone foam and a hardener, a curing condition, magnitude of the negative pressure or the positive pressure, a negative pressure or positive pressure time, and a depressurization start time or pressurization start time are adjusted, a foamed structure of the silicone foam can be changed to easily adjust characteristics such as weight, elasticity, a texture, hardness, and elongation, thereby manufacturing an implant according to the position and function in which the implant is to be applied in a human body.

DESCRIPTION OF DRAWINGS

FIG. 1 is a flowchart illustrating a method of manufacturing an implant for an implantation into a human body according to an embodiment of the present invention.

FIG. 2 is a schematic state diagram illustrating operation S120 shown in FIG. 1.

MODES OF THE INVENTION

Hereinafter, exemplary embodiments of the present invention will be described in detail with reference to the accompanying drawings.

FIG. 1 is a flowchart illustrating a method of manufacturing an implant for an implantation into a human body according to an embodiment of the present invention. Referring to FIG. 1, in the method for manufacturing the implant for the implantation into the human body, first, the mold 100 having a cavity 110 inside thereof is provided (S100).

Here, the mold 100 is a frame member which allows silicone foam 200 to be formed into a shape corresponding to a defective part of a human body later. The cavity 110 having a shape corresponding to the defective part of the human body is provided inside the mold 100.

The manufacture of the mold 100 will be described in more detail. First, an outer shape of an implant to be completed later is modeled based on a medical image acquired by photographing a part to be removed from the human body. Here, first, pre-modeling is performed on the implant so as to have a size and shape corresponding to the part to be removed from the human body, and then, a cavity 110 to be formed inside the mold 100 is modeled through post-modeling by which a surface area of an outer surface is modeled to be greater than that of the pre-modeled shape. Thus, the mold 100 is manufactured to have an inner space corresponding to the modeled shape. In this case, an inflow and outflow hole 120 may be formed to pass through one side of the mold 100 such that the cavity 110 of the mold 100 is connected to the outside of the mold 100. Here, the mold 100 may be formed as one structure, but the present invention is not limited thereto. Of course, the mold 100 may be formed by coupling a plurality of structures so as to be in contact with each other in a state in which the structures face each other. In this case, the mold 100 may be manufactured using a three-dimensional (3D) printer.

A surface post-treatment process of improving an inner surface in which the cavity 110 is formed may be performed on the manufactured mold 100, and then, a cleaning operation may be additionally performed using a cleaning solution. In this case, the cleaning solution may be an alcohol-based liquid such as isopropanol but is not limited thereto.

After the mold 100 is provided, the silicone foam 200 is injected into the cavity 110 formed inside the mold 100 (S110). That is, while the silicone foam 200 is cured in a state of being insertion-disposed to correspond to the cavity 110 of the mold 100, an exterior of the silicone foam 200 is molded into a shape corresponding to an inner shape of the mold 100, and more desirably, a shape corresponding to the cavity 110. Thus, the silicone foam 200 has a shape and size so as to be implantable into the human body by replacing the defective part of the human body. Here, of course, medical silicone should be used as the silicone foam 200.

In this case, before the silicone foam 200 is injected into the cavity 110 of the mold 100, a release agent (not shown) may be applied on the inner surface of the mold 100. The release agent allows the cured silicone foam 200 to be stably removed from the mold 100 later. Here, a product usable for a medical purpose may be selected and used as the release agent.

In addition, a hardener may be additionally mixed into the silicone foam 200 injected into the mold 100 may be further cured by mixing a curing agent. Thus, afterward, curing may be rapidly performed inside the mold 100, and a completed shape may also be stably maintained. Here, characteristics such as weight, elasticity, a texture, hardness, and elongation of a completed implant may be adjusted according to the mixing ratio of the hardener. In this case, the hardener may be mixed in a mixing ratio of 20 wt % to 80 wt % to 20 wt % to 80 wt % of the silicone foam. As a ratio of the hardener is increased, characteristics of the hardener are changed in such a manner that elasticity of the hardener is increased and elongation thereof is decreased. When the mixing ratio of the hardener to the silicone foam 200 is adjusted based on a basic mixing ratio of 50 wt % of the hardener to 50 wt % of the silicone foam, changes in characteristics such as elasticity, texture, hardness, and elongation may be adjusted in a range of 20% to 500%.

After the silicone foam 200 is injected into the cavity of the mold 100, pressure such as negative pressure or positive pressure is applied to the silicone foam 200 to generate a bubble 200 in the silicone foam 200 and then cure the silicone foam 200 (S120). That is, in a state in which the mold 100 into which the silicone foam 200 is injected is introduced into a pressure vessel, a negative pressure of 0.01 torr to 2,100 torr is applied to the silicone foam 200 for 300 seconds, and the silicone foam 200 is heated at a temperature of 25° C. to 250° C. and is cured.

In this case, elasticity, ductility, and elongation of the completed implant may be adjusted according to magnitude of the negative pressure or positive pressure, a negative pressure or positive pressure time, and a curing temperature. In this case, when descriptions are provided based on the negative pressure, as the magnitude of the negative pressure is decreased, the elasticity of the implant is increased, and the ductility and elongation thereof are decreased. As the magnitude of the negative pressure is increased, the elasticity of the implant is decreased, and the ductility and elongation thereof are increased. A size of the bubble 210 and a film thickness between the bubbles 210 in the completed implant are adjusted according to a depressurization start time and a negative pressure time. As the depressurization start time is delayed, the negative pressure time is shortened. Thus, the elasticity of the implant is increased, and the ductility and elongation thereof are decreased. On the contrary, as the depressurization start time is moved up, the negative pressure time is increased. Thus, the elasticity of the implant is decreased, and the ductility and elongation thereof are increased. Finally, a curing temperature adjusts a curing time of the completed implant. As the curing temperature is lowered, the curing time is increased. Thus, the elasticity of the implant is decreased, and the ductility and elongation thereof are increased. On the contrary, as the curing temperature is raised, the curing time is decreased. Thus, the elasticity of the implant is increased, and the ductility and elongation thereof are decreased. More specifically, when an implant for an implantation into a human body having an elasticity value smaller than a preset reference elasticity value is manufactured, negative pressure lower than preset reference negative pressure is applied. When an implant for an implantation into a human body having an elasticity value greater than the reference elasticity value is manufactured, negative pressure higher than the reference negative pressure is applied. When the implant for the implantation into the human body having the elasticity value smaller than the preset reference elasticity value is manufactured, a time during which negative pressure is applied is longer than a preset reference time. When the implant for the implantation into the human body having the elasticity value greater than the reference elasticity value is manufactured, a time during negative pressure is applied is shorter than the preset reference time. Finally, when an implant for an implantation into a human body having increased ductility and elongation is manufactured, negative pressure higher than the preset reference negative pressure is applied. When an implant for an implantation into a human body having decreased ductility and elongation is manufactured, negative pressure lower than the preset reference negative pressure is applied.

As described above, in a state in which the silicone foam 200 is injected into the mold 100, after the silicone foam 200 is cured to have a shape corresponding to the cavity 110 of the mold 100, the mold 100 is removed (S130). As described above, when the mold 100 is removed, an implant for an implantation into a human body having an outer shape corresponding to the part to be removed of the human body is completed. The completed implant for the implantation into the human body is cleaned again using an alcohol-based cleaning solution such as isopropanol to remove the release agent attached to a surface of the implant.

As described above, even when the implant for the implantation into the human body is not filled with a filling material, due to a support structure through the film between the bubbles 210 inside the silicone foam 200 and air inside the bubble 210 formed inside the silicone foam 200, elasticity may be maintained to maintain a stable shape even without the filling material, and the implant may have light weight and may be economically manufactured. Even when the implant is used for a long time in a state of being insertion-installed in a human body, there is no leakage filling material, thereby preventing a disease caused by the filling material.

In addition, the implant for the implantation into the human body according to the embodiment, after the silicone foam 200 is injected into the cavity 110 of the mold 100, negative pressure may be applied to form the bubble 210 inside the silicone foam 200. When a ratio of the hardener, a curing condition, magnitude of the negative pressure, a negative pressure time, and a depressurization start time are adjusted, a foamed structure of the silicone foam 200 may be changed to easily adjust characteristics such as weight, elasticity, a texture, hardness, and elongation, thereby manufacturing an implant according to a position and a function in which the implant is to be applied in a human body.

Although the present invention has been described with reference to the embodiments shown in the drawings, it should be understood by those skilled in the art that various changes and modifications may be made thereto and other embodiments equivalent thereto are possible. Therefore, the true scope of the present invention should be determined by the technical idea of the appended claims.

The invention claimed is:

1. A method of manufacturing an implant for implantation into a human body, the method comprising:
    preparing a mold having an inner cavity corresponding to a defective part in the human body;
    injecting silicone foam into the inner cavity of the mold;
    curing the silicone foam injected into the inner cavity of the mold by applying a negative pressure, wherein the cured silicone foam comprises more than one bubble; and
    removing the mold to form the implant,
    wherein an elasticity of the implant is determined by a size of the more than one bubble in the implant and a film thickness between the more than one bubble in the implant,
    wherein the size of the more than one bubble and the film thickness between the more than one bubble in the implant is adjusted during the curing of the silicone foam,
    wherein the curing silicone foam comprises:
        moving up a depressurization start time for manufacturing the implant having an elasticity value smaller than a preset reference elasticity value, wherein as the depressurization start time is moved up, the negative pressure time is applied early in a curing period and the implant having the elasticity value smaller than the preset reference elasticity value is formed, or
        delaying the depressurization start time for manufacturing the implant having the elasticity value greater than the preset reference elasticity value, wherein as the depressurization start time is delayed, the negative pressure time is applied late in the curing period and the implant having the elasticity value greater than the preset reference elasticity value is formed.

2. The method of claim 1, wherein the preparing the mold comprises modeling a shape based on a medical image acquired by photographing the defective part to be removed from the human body, and manufacturing the mold having the inner cavity corresponding to the modeled shape.

3. The method of claim 2, wherein, in the manufacturing of the mold having the inner cavity corresponding to the modeled shape, the mold is manufactured using a three-dimensional (3D) printer.

4. The method of claim 1, wherein the injecting the silicone foam comprises:
    adding a hardener to the said silicone foam and mixing in a range of 20 wt % to 80 wt % of the hardener with respect to a range of 20 wt % to 80 wt % of the said silicone foam.

5. The method of claim 1, wherein, in the curing the silicone foam,
    a negative pressure of 0.01 ton to 2100 ton is applied to the said silicone foam for 1 to 300 seconds, and the silicone foam is heated at a temperature of 25° C. to 250° C. to be cured.

6. The method of claim 1, wherein, in the curing the silicone foam:
    when the implant having the elasticity value smaller than the preset reference elasticity value is manufactured, negative pressure lower than a preset reference negative pressure is applied; and
    when the implant having the elasticity value greater than the preset reference elasticity value is manufactured, negative pressure higher than the preset reference negative pressure is applied.

7. The method of claim 1, wherein, in the curing the silicone foam:
    when the implant having the elasticity value smaller than the preset reference elasticity value is manufactured, the total time during which the negative pressure is applied is longer than a preset reference time; and when the implant having the elasticity value greater than the preset reference elasticity value is manufactured, the total time during which the negative pressure is applied is shorter than the preset reference time.

8. The method of claim 1, wherein, in the curing the silicone foam:

when an implant having increased ductility and elongation is manufactured, negative pressure higher than a preset reference negative pressure is applied, and when an implant having decreased ductility and elongation is manufactured, negative pressure lower than the preset reference negative pressure is applied.

9. The method of claim 1, wherein in the moving up the depressurization start time for manufacturing the implant having the elasticity value smaller than the preset reference value, the negative pressure is applied starting at a first half of a total curing time period of the silicone foam, and wherein in the delaying the depressurization start time for manufacturing the implant having the elasticity value greater than the preset reference elasticity value, the negative pressure is applied starting a second half of the total curing time period of the silicone foam.

* * * * *